US00PP32164P2

(12) United States Plant Patent
Kolster et al.

(10) Patent No.: US PP32,164 P2
(45) Date of Patent: Sep. 8, 2020

(54) ***HYDRANGEA* PLANT NAMED 'HORTMAFARFA'**

(50) Latin Name: *Hydrangea macrophylla*
Varietal Denomination: Hortmafarfa

(71) Applicants: KOLSTER HOLDING B.V., Boskoop (NL); HORTEVE BREEDING B.V., Aalsmeer (NL)

(72) Inventors: Peter R. Kolster, Boskoop (NL); Cornelis P. Eveleens, Aalsmeer (NL)

(73) Assignees: Kolster Holding B.V., Baskoop (NL); Horteve Breeding B.V., Aalsmeer (NL)

( * ) Notice: Subject to any disclaimer, the term of this patent is extended or adjusted under 35 U.S.C. 154(b) by 0 days.

(21) Appl. No.: 16/602,297

(22) Filed: Sep. 6, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Hydrangea* plant named 'Hortmafarfa', characterized by its upright to outwardly spreading plant habit; moderately vigorous to vigorous growth habit and moderate growth rate; freely branching habit with strong and thick sturdy stems; freely flowering habit; large mophead-type inflorescences with double-type flower that are bright pink in color; and good postproduction longevity.

2 Drawing Sheets

Figure 1:
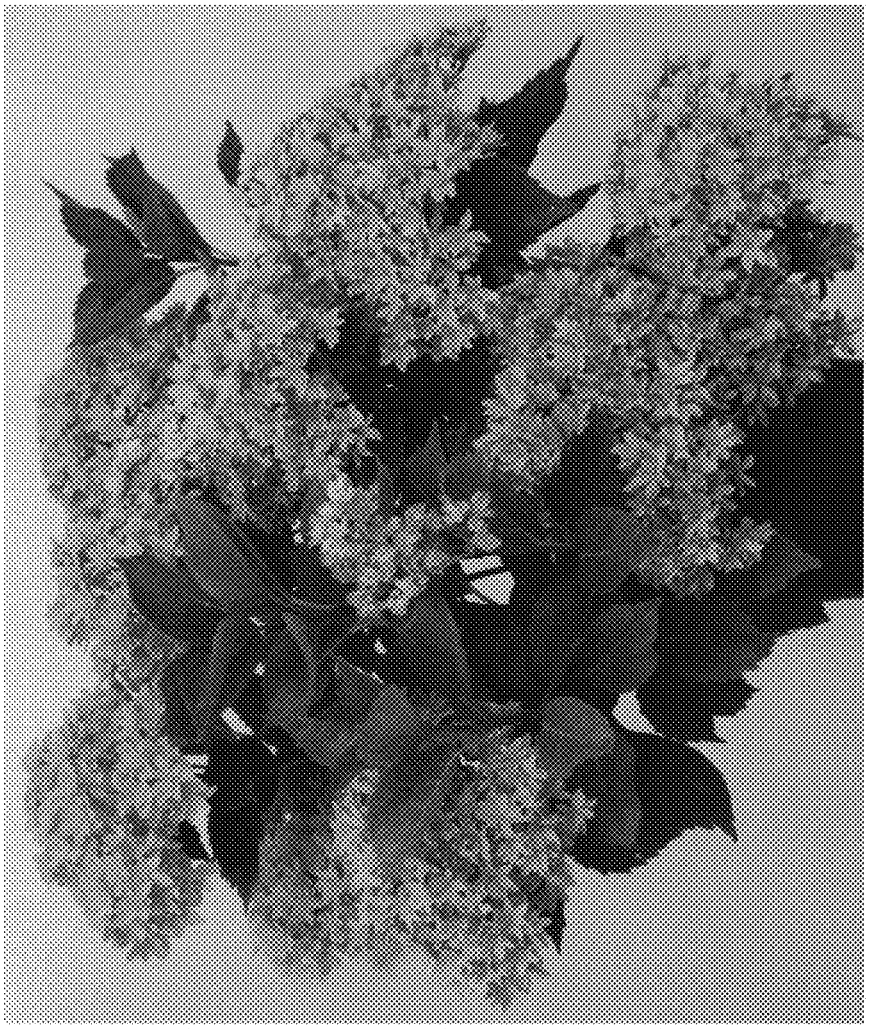

Botanical designation: *Hydrangea macrophylla.*
Cultivar denomination: 'HORTMAFARFA'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hortmafarfa'.

The new *Hydrangea* plant is a product of a planned breeding program conducted by the Inventors in Boskoop, The Netherlands. The objective of the breeding program was to create new potted *Hydrangea* plants with large showy inflorescences with numerous attractive double sterile flowers and good postproduction longevity.

The new *Hydrangea* plant originated from a cross-pollination made by the Inventors on Jun. 5, 2011 in Boskoop, The Netherlands, of a proprietary selection of *Hydrangea macrophylla* identified as code number 08-021-04, not patented, as the female, or seed, parent with a proprietary selection of *Hydrangea macrophylla* identified as code number 08-022-02, not patented, as the male, or pollen, parent. The new *Hydrangea* plant was discovered and selected by the Inventors as a single flowering plant from within the progeny of the stated cross-pollination in a controlled greenhouse environment in Boskoop, The Netherlands in June, 2013.

Asexual reproduction of the new *Hydrangea* plant by vegetative terminal cuttings in a controlled environment in Boskoop, The Netherlands since August, 2013 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hortmafarfa'. These characteristics in combination distinguish 'Hortmafarfa' as a new and distinct *Hydrangea* plant:

1. Upright to outwardly spreading plant habit.
2. Moderately vigorous to vigorous growth habit and moderate growth rate.
3. Freely branching habit with strong and thick sturdy stems.
4. Freely flowering habit.
5. Large mophead-type inflorescences with double-type flower that are bright pink in color.
6. Good postproduction longevity.

Plants of the new *Hydrangea* can be compared to plants of the female parent selection. Plants of the new *Hydrangea* differ primarily from plants of the female parent selection in the following characteristics:

1. Plants of the new *Hydrangea* have double-type flower whereas plants of the female parent selection have single and double-type flowers.
2. Sterile flower sepals of plants of the new *Hydrangea* are darker pink in color than sterile flower sepals of plants of the female parent selection.

Plants of the new *Hydrangea* can be compared to plants of the male parent selection. Plants of the new *Hydrangea* differ primarily from plants of the male parent selection in the following characteristics:

1. Plants of the new *Hydrangea* have double-type flower whereas plants of the male parent selection have single-type flowers.

2. Sterile flower sepals of plants of the new *Hydrangea* are lighter pink in color than sterile flower sepals of plants of the male parent selection.

Plants of the new *Hydrangea* can be compared to plants of *Hydrangea macrophylla* 'Hortdodapi', not patented. Plants of the new *Hydrangea* differ primarily from plants of 'Hortdodapi' in sterile flower color as sterile flower sepals of plants of the new *Hydrangea* are lighter pink in color than sterile flower sepals of plants of 'Hortdodapi'.

Plants of the new *Hydrangea* can be compared to plants of *Hydrangea macrophylla* 'Hort 10-087-07', disclosed in U.S. Plant Pat. No. 29,097. Plants of the new *Hydrangea* differ primarily from plants of 'Hort 10-087-07' in sterile flower color as sterile flower sepals of plants of the new *Hydrangea* are lighter pink in color than sterile flower sepals of plants of 'Hort 10-087-07'. In addition, inflorescences of plants of the new *Hydrangea* have more sterile flowers than inflorescences of plants of 'Hort 10-087-07'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'Hortmafarfa' grown in a container.

Figure 2:
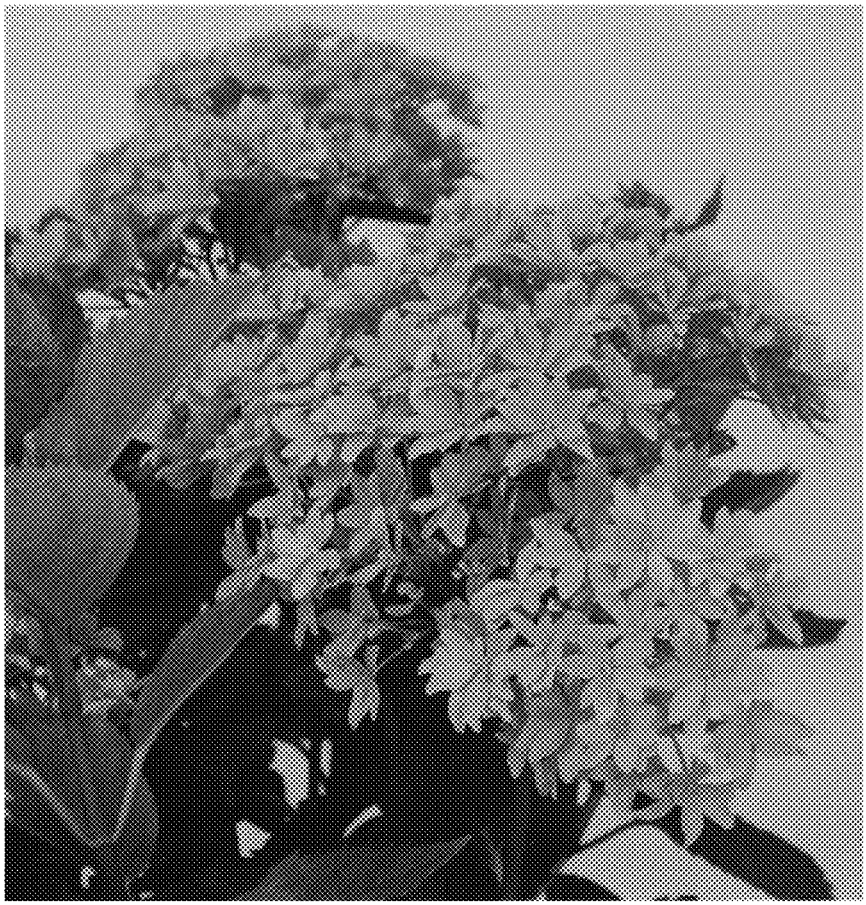

The photograph on the second sheet (FIG. 2 of 2) is a close-up view of a typical flowering plant of 'Hortmafarfa'.

DETAILED BOTANICAL DESCRIPTION

Plants used in the aforementioned photographs and in the following description were grown during the summer in 17-cm containers in a glass-covered greenhouse in Boskoop, The Netherlands and under cultural practices typical of commercial *Hydrangea* production. During the production of the plants, day temperatures ranged from 20° C. to 35° C. and night temperatures ranged from 10° C. to 22° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hortmafarfa'.

Parentage:

*Female, or seed, parent*.—Proprietary selection of *Hydrangea macrophylla* identified as code number 08-021-04, not patented.

*Male, or pollen, parent*.—Proprietary selection of *Hydrangea macrophylla* identified as code number 08-022-02, not patented Propagation:

*Type cutting*.—By vegetative terminal cuttings.

*Time to initiate roots, summer*.—About four weeks at temperatures about 15° C. to 25° C.

*Time to initiate roots, winter*.—About six weeks at temperatures about 15° C. to 21° C.

*Time to produce a rooted young plant, summer*.—About 100 days at temperatures about 15° C. to 25° C.

*Time to produce a rooted young plant, winter*.—About 140 days at temperatures about 15° C. to 21° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright to outwardly spreading plant habit; overall plant shape, globular; strong and sturdy lateral branches; moderately vigorous to vigorous growth habit and moderate growth rate.

*Plant height*.—About 44.5 cm.

*Plant diameter or area of spread*.—About 63.5 cm.

Lateral branch description:

*Branching habit*.—Freely branching habit about 24 lateral branches develop per plant; pinching will enhance branching.

*Length*.—About 23 cm.

*Diameter*.—About 5 mm.

*Internode length*.—About 4.5 cm.

*Texture*.—Smooth, glabrous; fully developed, woody.

*Aspect*.—Varying from upright to about 50° from vertical.

*Strength*.—Strong, sturdy.

*Color*.—When developing: Close to 144A. Developed: Close to 144A; at the internodes, strongly tinged with close to N186C; when woody, close to 199A to 199C and N199D.

*Lenticels*.—None observed.

Leaf description:

*Arrangement*.—Opposite, simple.

*Length*.—About 10.9 cm.

*Width*.—About 7.1 cm.

*Shape*.—Broadly ovate.

*Apex*.—Apiculate, often moderately twisting.

*Base*.—Oblique to short attenuate.

*Margin*.—Coarsely serrate.

*Texture, upper surface*.—Smooth to slightly rugose, glabrous.

*Texture, lower surface*.—Smooth to moderately rugose, glabrous.

*Venation pattern*.—Pinnate.

*Color*.—Developing leaves, upper surface: Darker than 143A. Developing leaves, lower surface: Close to 146B and 146C. Fully expanded leaves, upper surface: Close to 137A; venation, close to 146D. Fully expanded leaves, lower surface: Close to between 138B and 146B; venation, close to 146D.

*Petioles*.—Length: About 1.9 cm. Diameter: About 3 mm. Texture and luster, upper surface: Smooth, glabrous; moderately glossy. Texture and luster, lower surface: Smooth, glabrous; slightly glossy. Color, upper and lower surfaces: Close to 145A; at the base, slightly tinged with close to N186C.

Flower description:

*Flower type and habit*.—Showy double-type sterile flowers and small inconspicuous fertile flowers arranged on mophead-type terminal panicles; panicles flattened globular in shape; fertile flowers face mostly upright and sterile flowers face upright to outwardly depending on their position in the inflorescence.

*Fragrance*.—None detected.

*Natural flowering season*.—Plants flower from late spring to late summer in The Netherlands.

*Flower longevity*.—Fertile flowers last about three days on the plant, fertile flowers not persistent; sterile flowers last about six weeks on the plant, sterile flowers persistent.

*Quantity of flowers*.—Freely flowering habit; about 30 fertile flowers per panicle and about 200 sterile flowers per panicle.

*Panicle height*.—About 15.9 cm.

*Panicle diameter*.—About 17.7 cm.

*Fertile flower buds*.—Length: About 6 mm. Diameter: About 4 mm. Shape: Cup-shaped. Color: Close to 58C.

*Sterile flower buds*.—Length: About 1 cm. Diameter: About 1.5 cm. Shape: Cup-shaped. Color: Close to 145C; distally, close to 52C.

*Fertile flower diameter*.—About 2 cm.

*Fertile flower depth* (*height*).—About 1.3 mm.

*Sterile flower diameter*.—About 3 cm.

*Sterile flower depth* (*height*).—About 1.3 cm.

*Petals, fertile flowers*.—Quantity and arrangement: About three to seven in a single whorl. Length: About 1.1 cm. Width: About 6 mm. Shape: Narrowly ovate to narrowly elliptic. Apex: Narrowly obtuse to bluntly acute. Base: Cuneate. Margin: Entire. Texture and luster, upper and lower surfaces: Smooth, glabrous; matte. Color: When opening, upper surface: Close to 52C to 52D; towards the base, close to 150D. When opening, lower surface: Close to 51D; towards the base, close to 150D. Fully opened, upper surface: Close to 64D; color becoming closer to 144B fading towards the apex to close to 144C with development. Fully opened, lower surface: Close to 65A; color becoming closer to 145B with development.

*Petals, sterile flowers*.—To date, petal development has not been observed on sterile flowers of plants of the new *Hydrangea*.

*Sepals, fertile flowers*.—Quantity and arrangement: About five in a single whorl. Length: About 2 mm. Width: About 0.75 mm. Shape: Obovate to elliptic. Apex: Acute. Base: Cuneate. Margin: Entire. Texture and luster, upper and lower surfaces: Smooth, glabrous; matte. Color: When opening and fully opened, upper surface: Close to 144B tinged with close to 59D; color does not change with development. When opening and fully opened, lower surface: Close to 144B tinged with close to 59D; color does not change with development.

*Sepals, sterile flowers*.—Quantity and arrangement: About eight to eleven in two whorls. Length: About 1.5 cm. Width: About 7 mm. Shape: Narrowly ovate to narrowly elliptic. Apex: Narrowly obtuse to bluntly acute. Base: Cuneate. Margin: Entire. Texture and luster, upper and lower surfaces: Smooth, glabrous; matte. Color: When opening, upper surface: Close to 52C to 52D; towards the base, close to 150D. When opening, lower surface: Close to 51D; towards the base, close to 150D. Fully opened, upper surface: Close to 64D; with development, color becoming close to 144B and distally, close to 144C. Fully opened, lower surface: Close to 65A; with development, color becoming closer to 145B.

*Pedicels, fertile flowers*.—Length: About 7 mm. Diameter: About 1 mm. Strength: Moderately strong. Aspect: Mostly upright. Texture and luster: Smooth, glabrous; matte. Color: Close to 59D.

*Pedicels, sterile flowers*.—Length: About 2.2 cm. Diameter: About 1.25 mm. Strength: Moderately strong. Aspect: About 45° from peduncle axis. Texture and luster: Sparsely pubescent; matte. Color: Close to 59D.

*Reproductive organs, fertile flowers*.—Stamens: To date, stamen development has not been observed on fertile flowers of plants of the new *Hydrangea*. Pistils: Pistil quantity per flower: About three, occasionally two or four. Pistil length: About 1 mm. Stigma shape: Club-shaped. Stigma color: Close to N155B. Style length: About 0.5 mm. Style color: Close to 182D. Ovary color: Close to 147D.

*Reproductive organs, sterile flowers*.—Stamens: To date, stamen development has not been observed on sterile flowers of plants of the new *Hydrangea*. Pistils: Pistil quantity per flower: About three, occasionally two. Pistil length: About 1 mm. Stigma shape: Club-shaped. Stigma color: Close to N155B. Style length: About 0.5 mm. Style color: Close to 182D. Ovary color: Close to 147D.

*Seeds*.—To date, seed development has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Temperature tolerance: Plants of the new *Hydrangea* have been observed to tolerate temperatures ranging from −20° C. to 35° C. and are suitable for USDA Hardiness Zones 5 to 9.

It is claimed:

1. A new and distinct *Hydrangea* plant named 'Hortmafarfa' as illustrated and described.

* * * * *